(12) United States Patent
Chakravorty et al.

(10) Patent No.: US 10,405,739 B2
(45) Date of Patent: Sep. 10, 2019

(54) AUTOMATICALLY DETECTING EYE TYPE IN RETINAL FUNDUS IMAGES

(71) Applicant: International Business Machines Corporation, Armonk, NY (US)

(72) Inventors: Rajib Chakravorty, Kingville (AU); Rahil Garnavi, Ivanhoe East (AU); Pallab Roy, Kingsville (AU)

(73) Assignee: International Business Machines Corporation, Armonk, NY (US)

( * ) Notice: Subject to any disclaimer, the term of this patent is extended or adjusted under 35 U.S.C. 154(b) by 131 days.

(21) Appl. No.: 15/047,734

(22) Filed: Feb. 19, 2016

(65) Prior Publication Data

US 2017/0112372 A1   Apr. 27, 2017

Related U.S. Application Data

(60) Provisional application No. 62/245,455, filed on Oct. 23, 2015.

(51) Int. Cl.
| | |
|---|---|
| *A61B 3/00* | (2006.01) |
| *G06K 9/00* | (2006.01) |
| *A61B 3/14* | (2006.01) |
| *A61B 3/12* | (2006.01) |
| *G06T 7/00* | (2017.01) |
| *G06N 3/02* | (2006.01) |

(52) U.S. Cl.
CPC .............. *A61B 3/0025* (2013.01); *A61B 3/12* (2013.01); *A61B 3/1241* (2013.01); *A61B 3/14* (2013.01); *G06K 9/00* (2013.01); *G06K 9/0061* (2013.01); *G06K 9/00617* (2013.01); *G06T 7/0012* (2013.01); *G06T 2207/30041* (2013.01)

(58) Field of Classification Search
CPC ......... A61B 3/152; A61B 3/12; A61B 3/0025; A61B 3/14; A61B 3/1233; A61B 3/1241; G06K 9/00597; G06K 9/00503; G06K 7/1482
USPC ............... 351/206, 210, 246, 245, 205, 208; 706/16, 25, 31, 934, 48, 44, 41, 38, 2, 6, 706/15
See application file for complete search history.

(56) References Cited

U.S. PATENT DOCUMENTS 9,462,945 B1 * 10/2016 Barriga .................. A61B 3/152
2014/0294235 A1 * 10/2014 Ishida .................. G06K 9/0061
382/103

OTHER PUBLICATIONS

Tan et al. "Automatic Detection of Left and Right Eye in Retinal Fundus Images" ICBME 2008, Proceedings 23, pp. 610-614, 2009.*
Chen et al. "Hierarchical Local Binary Pattern for Branch Retinal Vein Occlusion Recognition." Computer vision—ACCV Nov. 2014 Workshops pp. 687-697.*

(Continued)

*Primary Examiner* — Stephone B Allen
*Assistant Examiner* — Travis S Fissel

(57) ABSTRACT

A computer-implemented method includes obtaining an image of a retinal fundus. A plurality of features is extracted from the image of the retinal fundus. The plurality of features includes at least one feature based on anatomical domain knowledge of the retinal fundus and at least one response of a pre-trained deep convolutional neural network to at least a portion of the image of the retinal fundus. The retinal fundus is determined to belong to a left eye or a right eye, based on an analysis of the plurality of features.

19 Claims, 6 Drawing Sheets

(56) References Cited

OTHER PUBLICATIONS

Roth et al. "Medical Image Computing and Computer-Assisted Intervention" 17th International Conference, Boston, MA, USA, Sep. 14-18, 2014, Proceedings, Part I. pp. 520-527.*
Muthusamy et al. "Gradient based glaucoma detection by segmenting optic disc and cup" Intl. Journal of Software and Hardware Research in Engineering, ISSN No. 234-4890, vol. 2 Issue 2, Feb. 2014.*
Gonzalez et al. "Segmentation of the Blood Vessels and Optic Disk in Retinal Images," IEEE Journal of Biomedical and Health Informatics, vol. 18, No. 6, Nov. 2014.*
Tsung-Han et al. "PCANet: A Simple Deep Learning Baseline for Image Classification?" Journal of LATEX class files, Aug. 2014.*
STIC Search, Sep. 17, 2018.*
Fully Convolutional Networks for Semantic Segmentation, arXiv:1411.4038. Long et al. (Year: 2014).*
Li, Huiqi et al., "Automated feature extraction in color retinal images by a model based approach", Biobedical Engineering, IEEE transactions on vol. 51, No. 2, pp. 246-254, 2004.
Sinthanayothin, Chanjira et al., "Automated localization of the optic disc, fovea, and retinal blood vessels from digital colour fundus images", British Journal of Ophthalmology, vol. 83, No. 8, pp. 902-910, 1999.
Tamura, Shinichi et al., "Zero-crossing interval correction in tracing eye-fundus blood vessels," Pattern recognition, vol. 21, No. 3, pp. 227-233, 1998.
Tan, NM et al., "Automatic detection of left and right eye in retinal fundus images", in $13^{th}$ International Conference on Biomedical Engineering, Springer, pp. 610-614, 2009.
Vedaldi, Andrea et al., "Matconvnet-convolutional neural networks for matlab", arXiv preprint arXiv: 1412.4564, 2014.
Nguyen, Uyen TV et al.,"An effective retinal blood vessel segmentation method using multi-scale line detection", Pattern recognition, vol. 46, No. 3, pp. 703-715, 2013.
Krizhevsky Alex et al., Imagenet classification with deep convolutional neural networks:, in Advances in neural information processing systems, pp. 1097-1105, 2012.
Simonyan Karen et al., "Very deep convolutional networks for large-scale image recognition", arXiv preprint arXiv:1409.1556, 2014.
Suykens, Johan AK et al., "Drishti-gs Retinal image dataset for optic nerve head (onh) segmentation", I Biomedical Imaging (ISBI), IEEE $11^{th}$ International, 2014.

* cited by examiner

AUTOMATICALLY DETECTING EYE TYPE IN RETINAL FUNDUS IMAGES

BACKGROUND OF THE INVENTION

Ophthalmologists often use images of the retinal fundus (i.e., the interior lining of the eyeball, including the retina, the optic disc, and the macula) to diagnose and monitor the development of eye diseases. For example, retinal fundus imaging is one of the leading image technologies used for the diagnosis of diabetic retinopathy, age-related macular degeneration (DR), hypertensive retinopathy, and systemic diseases (e.g., stroke), among other conditions. The developments and applications of computer-aided diagnosis (CAD) systems for detecting different types of diseases in retinal imaging have been increasing rapidly in recent years.

SUMMARY OF THE INVENTION

A computer-implemented method includes obtaining an image of a retinal fundus. A plurality of features is extracted from the image of the retinal fundus. The plurality of features includes at least one feature based on anatomical domain knowledge of the retinal fundus and at least one response of a pre-trained deep convolutional neural network to at least a portion of the image of the retinal fundus. The retinal fundus is determined to belong to a left eye or a right eye, based on an analysis of the plurality of features.

In another example, a machine-readable storage medium is encoded with instructions executable by a processor. The instructions cause the processor to perform operations including obtaining an image of a retinal fundus. A plurality of features is extracted from the image of the retinal fundus. The plurality of features includes at least one feature based on anatomical domain knowledge of the retinal fundus and at least one response of a pre-trained deep convolutional neural network to at least a portion of the image of the retinal fundus. The retinal fundus is determined to belong to a left eye or a right eye, based on an analysis of the plurality of features.

In another example, a computer-implemented method includes cropping a region of interest from an image of a retinal fundus. A search region is defined within the region of interest, and a plurality of horizontal cross sections is defined with the search region. A plurality of votes for the plurality of horizontal cross sections is generated. A given vote of the plurality of votes indicates whether a corresponding cross section of the plurality of horizontal cross sections likely depicts a left eye or a right eye. A probability score is computed for the image of the retinal fundus, based on the plurality of votes. The probability score indicates a likelihood of the image of the retinal fundus depicting the left eye or the right eye.

BRIEF DESCRIPTION OF THE DRAWINGS

So that the manner in which the above recited features of the present invention can be understood in detail, a more particular description of the invention may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In one embodiment, a method, machine readable storage medium, and apparatus for automatically detecting eye type in retinal fundus images is disclosed. As discussed above, ophthalmologists often use images of the retinal fundus to diagnose and monitor the development of eye diseases. One important piece of metadata information that is relevant to the detection of diseases using retinal fundus images is eye type, i.e., whether a retinal fundus image depicts the retinal fundus of the left eye or of the right eye. For instance, light coming from anywhere in the left eye of the visual environment projects onto the left half-retinas, and that light information is sent to the left hemisphere of the brain. Similarly, light coming from anywhere in the right eye of the visual environment projects onto the right half-retinas, and that information is sent to the right hemisphere of the brain. Since the changes in the right and left hemispheres of the brain have different clinical significance, knowing whether a retinal fundus image depicts the left eye or the right eye can provide diagnostically helpful information.

Eye type is frequently detected manually after image acquisition; however, this approach is time consuming, expensive, and impractical for automatic mass screening and diagnosis of retinal diseases. Automatic methods for detecting eye type have also been proposed; however, these methods tend to be unreliable unless specific optic features (e.g., macula, retinal blood vessels, etc.) can be clearly identified in the images, which is not always the case.

Embodiments of the invention automatically detect eye type in retinal fundus images based on a combination of different anatomical domain knowledge. In one example, a set of customized anatomical features is used to map the anatomical properties of the left eye and the right eye. In further examples, a pre-trained deep convolutional neural network is used to learn the discriminative patterns of the left eye and the right eye. In this case, the combination of the customized set of anatomical features and the response of the deep convolutional neural network is used to train a support vector machine (SVM) to classify retinal fundus images according to the eye type depicted. The integration of the disclosed eye type detection system with a computer-aided diagnosis system will minimize manual interventions, thereby saving time and money.

Figure 1:
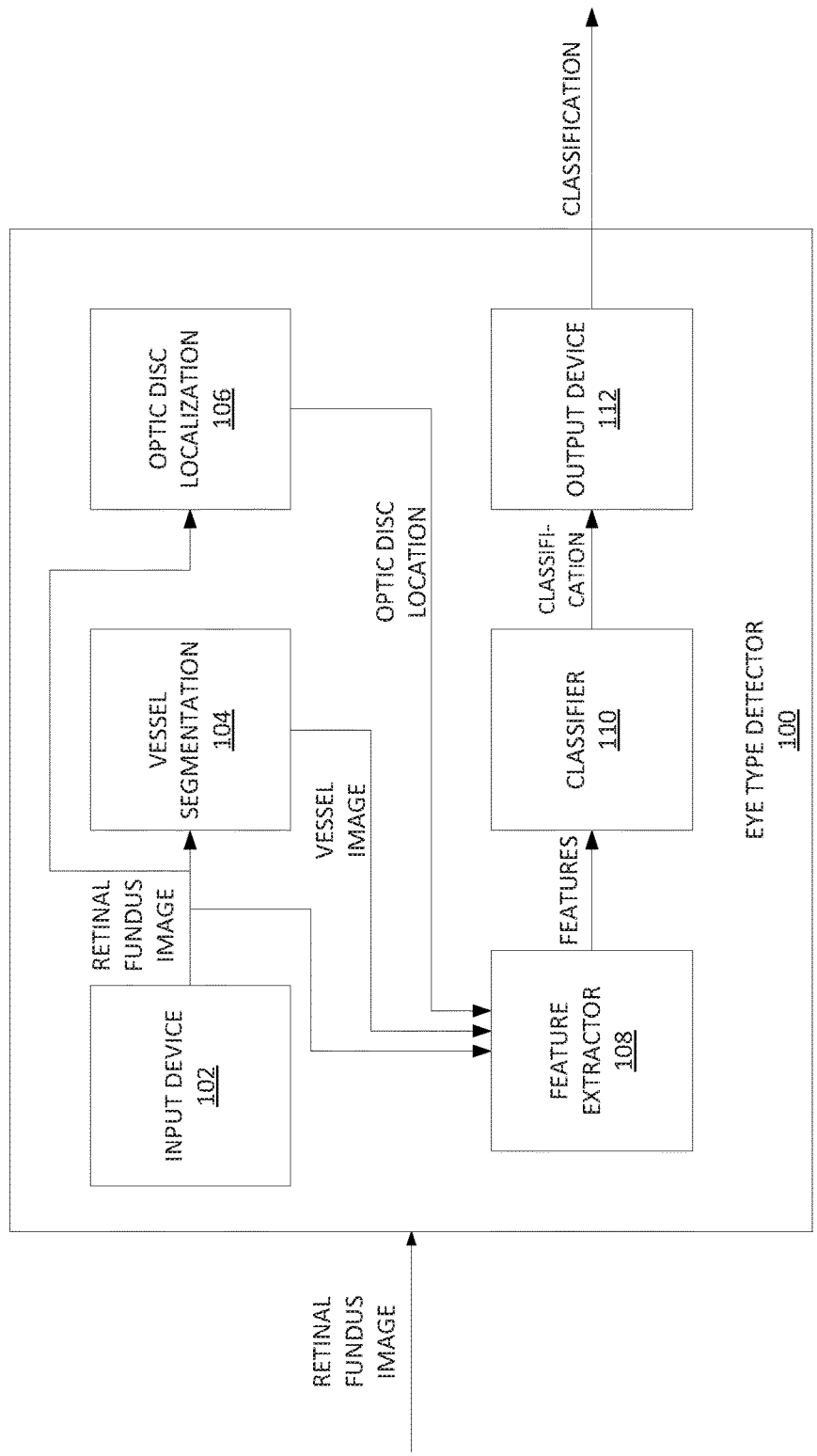
FIG. 1 is a high level block diagram illustrating one example of an eye type detector, according to the present disclosure.

FIG. 1 is a high level block diagram illustrating one example of an eye type detector 100, according to the present disclosure. The eye type detector 100 receives a retinal fundus image as input, and subsequently performs a plurality of operations on the retinal fundus image in order to automatically classify the eye type (i.e., left eye or right eye) depicted in the image. The eye type classification is output by the eye type detector 100, e.g., for further use in diagnosing and/or monitoring a health condition.

In one example, the eye type detector 100 generally comprises an input device 102, a vessel segmentation processor 104, an optic disc localization processor 106, a feature extractor 108, a classifier 110, and an output device 112.

The input device 102 may comprise any type of input device that is capable of receiving or selecting a retinal fundus image. For example, the input device 102 may comprise one or more of: an imaging sensor, a scanner, a network interface card, a receiver, an input port, a mouse, or a storage device, among other types of input devices. The input device 102 obtains a retinal fundus image that is to be classified and provides the image to other components of the eye type detector 100 for further processing.

The vessel segmentation processor 104 is communicatively coupled to the input device 102, from which it receives the retinal fundus image. The vessel segmentation processor 104 segments or extracts an image of the retinal blood vessels (e.g., arteries and veins) from the retinal fundus image. The vessel segmentation processor 104 is communicatively coupled to the feature extractor 108 and provides the segmented image of the retinal blood vessels to the feature extractor 108 for further processing.

The optic disc localization processor 106 is also communicatively coupled to the input device 102, from which it receives the retinal fundus image. The optic disc localization processor 106 locates the position of the optic disc (i.e., the raised disk on the retina at the point of entry of the optic nerve) in the retinal fundus image. The vessel segmentation processor 104 is communicatively coupled to the feature extractor 108 and provides the location of the optic disc to the feature extractor 108 for further processing.

The feature extractor 108 is communicatively coupled to the vessel segmentation processor 104 and the optic disc localization processor 106, from which it receives the segmented image of the retinal blood vessels and the location of the optic disc, respectively. The feature extractor 108 may also be communicatively coupled to the input device 102, from which it receives the retinal fundus image. The feature extractor 108 extracts one or more features from the retinal fundus image, based on the segmented image of the retinal blood vessels and the location of the optic disc. The extracted features are features that can help classify the type of the eye depicted in the retinal fundus image and may include both supervised and unsupervised features. In one example, the supervised features include anatomical domain knowledge-based features, while the unsupervised features include deep convolutional neural network-based features. For instance, the features extracted by the feature extractor 108 may include one or more of: a cross-sectional vote-based probability score, the blood vessel density on the left and right sides of the optic disc, the orientation of a major blood vessel with respect to the optic disc, and the response of a deep convolutional neural network. The feature extractor 108 is communicatively coupled to the classifier 110 and provides extracted features to the classifier 110 for further processing.

The classifier 110 is communicatively coupled to the feature extractor 108, from which it receives the extracted features. The classifier 110 uses the extracted features to classify the type (i.e., left eye or right eye) of the eye depicted in the input retinal fundus image. In one example, the classifier 110 includes a support vector machine (SVM) that has been trained using the types of features extracted by the feature extractor 108. The classifier 110 is communicatively coupled to the output device 112 and provides the classification of the input retinal fundus image to the output device 112.

The output device 112 is communicatively coupled to the classifier 110, from which it receives the classification of the input retinal fundus image. The output device may comprise any type of output device that is capable of providing a signal (e.g., indicating the classification) to a human operator and/or another device. For example, the output device 112 may comprise one or more of: a display, a speaker, a speech synthesizer, a network interface card, a transmitter, an output port, a haptic feedback device, or a storage device, among other types of output devices.

Figure 2:
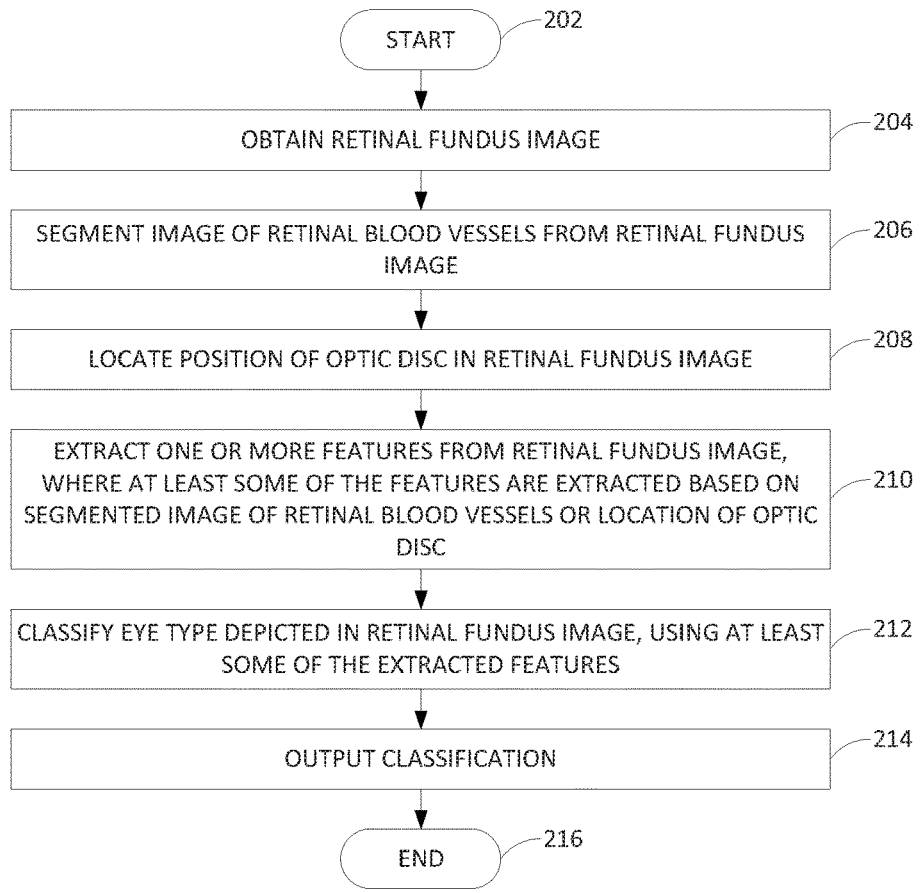
FIG. 2 is a flow diagram illustrating one example of a method for automatically detecting eye type in a retinal fundus image, according to the present disclosure.

FIG. 2 is a flow diagram illustrating one example of a method 200 for automatically detecting eye type in a retinal fundus image, according to the present disclosure. The method 200 may be performed, for example, by the eye type detector 100 illustrated in FIG. 1. As such, reference is made in the discussion of the method 200 to various components of the eye type detector 100. However, the method 200 could also be performed by a system that is configured in a different manner. Thus, the references to the components of the eye type detector 100 in the following discussion are not intended to be limiting.

The method 200 begins in step 202. In step 204, the input device 102 obtains a retinal fundus image. The retinal fundus image depicts the retinal fundus (i.e., the interior lining of the eyeball, including the retina, the optic disc, and the macula) of an eye (e.g., a human eye). In one example, the retinal fundus image is a color image.

In step 206, the vessel segmentation processor 104 segments an image of the retinal blood vessels (e.g., arteries and veins) from the retinal fundus image. In one example, this segmentation is achieved by first enhancing the retinal blood vessels in the retinal fundus image, for example using a multi-scale line detection method. Image thresholding may subsequently be applied to segment an image of the enhanced retinal blood vessels from the retinal fundus image.

In step 208, the optic disc localization processor 106 locates the position of the optic disc (i.e., the raised disk on the retina at the point of entry of the optic nerve) in the retinal fundus image. In one example, locating the optic disc is achieved by first generating a green channel retinal image from the retinal fundus image. In color/RGB retinal fundus images, the green channel often displays the best contrast between the retinal blood vessels and the background. A non-overlapping sliding window approach may then be applied on the green channel retinal image and on the corresponding binary blood vessel mask to locate the position of the optic disc. In one example, the sliding window with the maximum blood vessel density and the maximum intensity value is selected as the likely location of the optic disc.

In step 210, the feature extractor 108 extracts one or more features from the retinal fundus image, based on the segmented image of the retinal blood vessels and the location of the optic disc. The extracted features may include both supervised and unsupervised features. In one example, the supervised features include anatomical domain knowledge-based features, while the unsupervised features include deep convolutional neural network-based features. For instance, the features extracted by the feature extractor 108 may include one or more of: a cross-sectional vote-based probability score, the blood vessel density on the left and right sides of the optic disc, the orientation of a major blood vessel with respect to the optic disc, and the response of a deep convolutional neural network. Example methods for extracting these features are discussed in greater detail in connection with FIGS. 3-6.

In step 212, the classifier 110 classifies the type (i.e., left eye or right eye) of the eye depicted in the retinal fundus image, using at least some of the features extracted by the feature extractor 108 in step 210. In one example, the classifier 110 includes a support vector machine (SVM) that has been trained using the types of features extracted by the feature extractor 108. In one example, the optimal hyper parameters of the SVM classifier are computed using a five-fold cross validation accuracy-based grid search over a validation dataset. In one example validation dataset, the optimally selected hyper parameters are: C=10; degree=3; gamma=0.1; kernel=polynomial; and tolerance=0.001.

In step 214, the output device 112 outputs the classification produced in step 212. For instance, the output device 112 may display the classification on a display or may send a signal over a network to another device or system, where the signal includes the classification.

The method 200 ends in step 216.

Experimental results have shown that the method 200, which performs classification based on a combination of anatomical domain knowledge-based features and deep convolutional neural network-based response features, achieves a statistical $F_1$ score of approximately 0.87. In this case, the precision (i.e., the number of correct positive results divided by the number of all positive results) is approximately 0.88, and the recall (i.e., the number of correct positive results divided by the number of positive results that should have been returned) is approximately 0.85. This performance is a significant improvement over conventional methods for automatic eye type detection, which have been experimentally shown to achieve statistical $F_1$ scores up to approximately 0.79.

Figure 3:
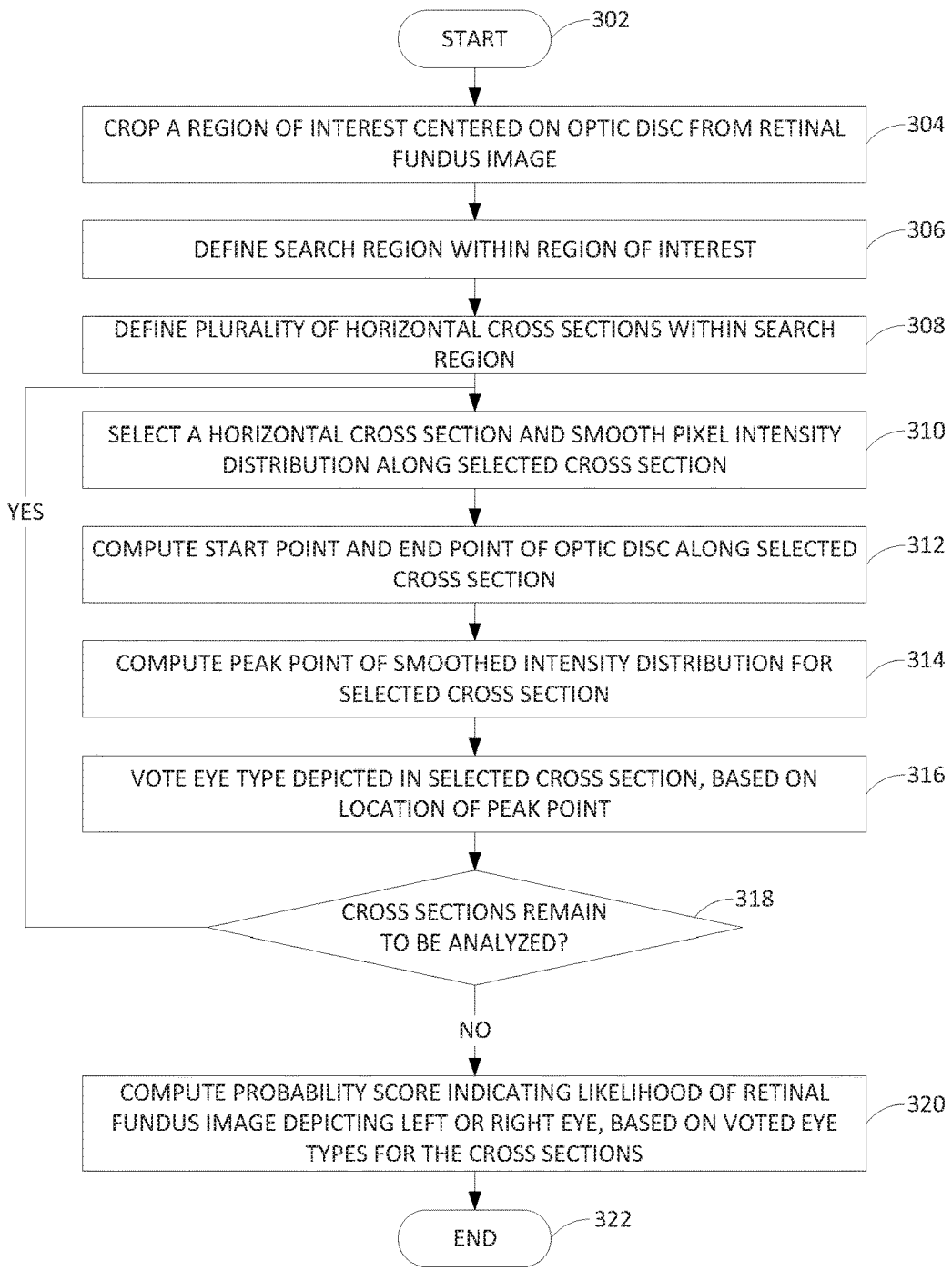
FIG. 3 is a flow diagram illustrating one example of a method for computing a cross-sectional vote-based probability score of a retinal fundus image, according to the present disclosure.

FIG. 3 is a flow diagram illustrating one example of a method 300 for computing a cross-sectional vote-based probability score of a retinal fundus image, according to the present disclosure. The cross-sectional vote-based probability score exploits information about various sectors of a retinal fundus (e.g., superior sector, temporal sector, inferior sector, nasal sector) in order to compute a probability that a given retinal fundus is part of the right eye or the left eye. For instance, in a retinal fundus image of a left eye, the temporal sector will be located on the right side of the image, while in a retinal fundus image of the right eye, the temporal sector will be located on the left side of the image. Moreover, the temporal sector of the optic disc tends to display a higher pixel intensity than the nasal sector.

The method 300 may be performed, for example, by the feature extractor 108 of the eye type detector 100 (e.g., in conjunction with step 210 of the method 200). As such, and for the sake of example, reference is made in the discussion of the method 300 to the feature extractor 108. However, the method 300 could also be performed by a different component of the eye type detector 100, or by a different system entirely. Thus, the references to the feature extractor 108 in the following discussion are not intended to be limiting.

The method 300 begins in step 302. In step 304, the feature extractor 108 obtains a candidate location of the optic disc (e.g., as identified by the optic disc localization processor 106) and crops a preliminary region of interest (ROI) of size W×W centered on the candidate location from the retinal fundus image. In one example, the preliminary region of interest is rectangular in shape (e.g., 300 pixels× 300 pixels). In one example, after cropping the preliminary region of interest, a circular Hough transform is applied on the red channel of the preliminary region of interest to estimate the center and radius (r) of the optic disc. The size of the preliminary region of interest is then updated using the estimated optic disc center and radius to produce an updated region of interest. In one example, the updated region of interest is centered on the optic disc center, and the size of updated region of interest is set to P×P, where P=2r.

In step 306, the feature extractor 108 defines a search region within the updated region of interest. In one example, the search region includes a region that extends a predefined number of pixels above and below the center of the optic disc. For instance, if the average diameter of the optic disc is assumed to be approximately eighty pixels, the search region might extend fifty pixels above and fifty pixels below the center of the optic disc (since a search region thus defined should cover the majority of the optic disc).

In step 308, the feature extractor 108 defines a plurality of horizontal cross sections or rows from the updated region of interest. In one example, the index of the starting cross section is $R_{c-n}$, and the index of the ending cross section if $R_{c+n}$, where c is the index of the cross section passing through the center of the optic disc, n=r*a, and a=0.65. Thus, the total number of cross sections defined is 2n in one example. Each cross section within these boundaries is analyzed by the feature extractor 108. In one example, n is chosen to be smaller than r to restrict the search region inside the optic disc, because the intensity information outside of the optic disc may add noise in the extracted features.

In step 310, the feature extractor 108 selects a horizontal cross section and smoothes the pixel intensity distribution along the selected cross section. For instance, the feature extractor 108 may map the position of each pixel in the selected cross section against that pixel's raw intensity to generate an initial pixel intensity distribution. The initial pixel intensity distribution may then be smoothed, for example by applying a local averaging filter (e.g., of size 25×1) to remove noise.

In step 312, the feature extractor 108 computes the start point and the end point of the optic disc along the selected cross section. In one example, the start point and the end point of the optic disc are computed by analyzing the gradient of the pixel intensity values, and selecting the highest point along the gradient as the start point and the lowest point along the gradient as the end point. The middle point between the start point and the end point can subsequently be used to compute the center of the optic disc for the selected cross section.

In step 314, the feature extractor 108 computes the peak point of the smoothed intensity distribution for the selected cross section (e.g., the pixel position with the highest smoothed intensity value).

In step 316, the feature extractor 108 votes the eye type depicted in the selected cross section, based on the location of the peak point computed in step 314. In one example, the feature extractor 108 will vote for the left eye if the peak point is located to the right of the optic disc center (as computed in step 312). Conversely, the feature extractor 108 will vote for the right eye if the peak point is located to the left of the optic disc center.

In step 318, the feature extractor 108 determines whether there are any horizontal cross sections remaining to be analyzed. If the feature extractor 108 concludes in step 318 that there are additional horizontal cross sections to be analyzed, then the method 300 returns to step 310, the feature extractor 108 selects another (not previously analyzed) horizontal cross section, and steps 310-316 are repeated for the newly selected cross section.

Once the feature extractor concludes in step 318 that all of the horizontal cross sections have been analyzed, the method 300 proceeds to step 320. In step 320, the feature extractor 108 computes a probability score indicating the likelihood that the retinal fundus image depicts the right eye and/or the left eye. In one example, the probability score is computed based on the votes (as generated in step 316) for all of the horizontal cross sections in the search region. For instance, in one case, the probability score for a given eye (right or left) is computed as a percentage of the votes favoring the given eye (e.g., if seven out of ten votes favored the left eye, and three out of the ten votes favored the right eye, then the probability score for the left eye would be 0.7, and the probability score for the right eye would be 0.3).

The method 300 ends in step 322.

Figure 4:
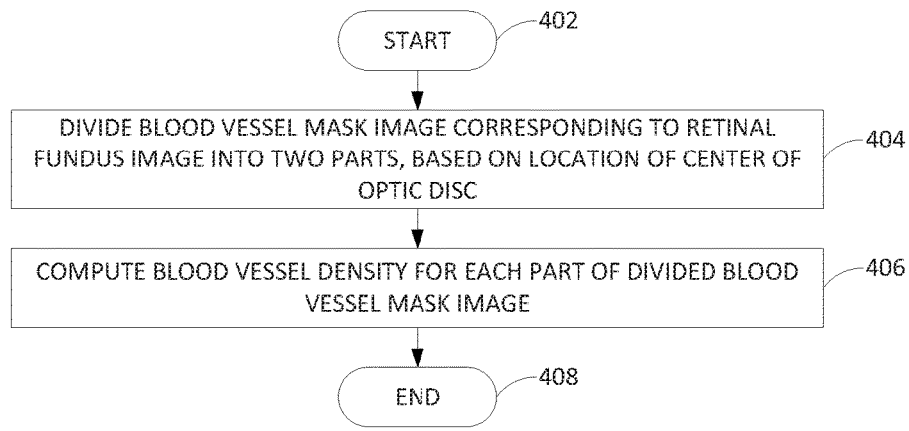
FIG. 4 is a flow diagram illustrating one example of a method for computing a retinal blood vessel density of a retinal fundus image, according to the present disclosure.

FIG. 4 is a flow diagram illustrating one example of a method 400 for computing a retinal blood vessel density of a retinal fundus image, according to the present disclosure. The method 400 encodes anatomical properties regarding blood vessel density in the fovea centralis (or fovea) into a feature vector that can be used to discriminate between the left eye and the right eye in retinal fundus images. The fovea (i.e., the small pit located in the center of the macula lutea) is responsible for central vision and thus contains the highest concentration of rod and cone cells in the retina. The fovea is located in the temporal sector of the retina, where the blood vessel density tends to be lower (e.g., as compared to the nasal sector).

The method 400 may be performed, for example, by the feature extractor 108 of the eye type detector 100 (e.g., in conjunction with step 210 of the method 200). As such, and for the sake of example, reference is made in the discussion of the method 400 to the feature extractor 108. However, the method 400 could also be performed by a different component of the eye type detector 100, or by a different system entirely. Thus, the references to the feature extractor 108 in the following discussion are not intended to be limiting.

The method 400 begins in step 402. In step 404, the feature extractor 108 divides a blood vessel mask image corresponding to the retinal fundus image into two parts, based on the location of the center of the optic disc. In one example, the blood vessel mask image is divided along a vertical line that passes through the center of the optic disc.

In step 406, the feature extractor 108 computes the blood vessel density for each part of the divided blood vessel mask image.

The method 400 ends in step 408.

Figure 5:
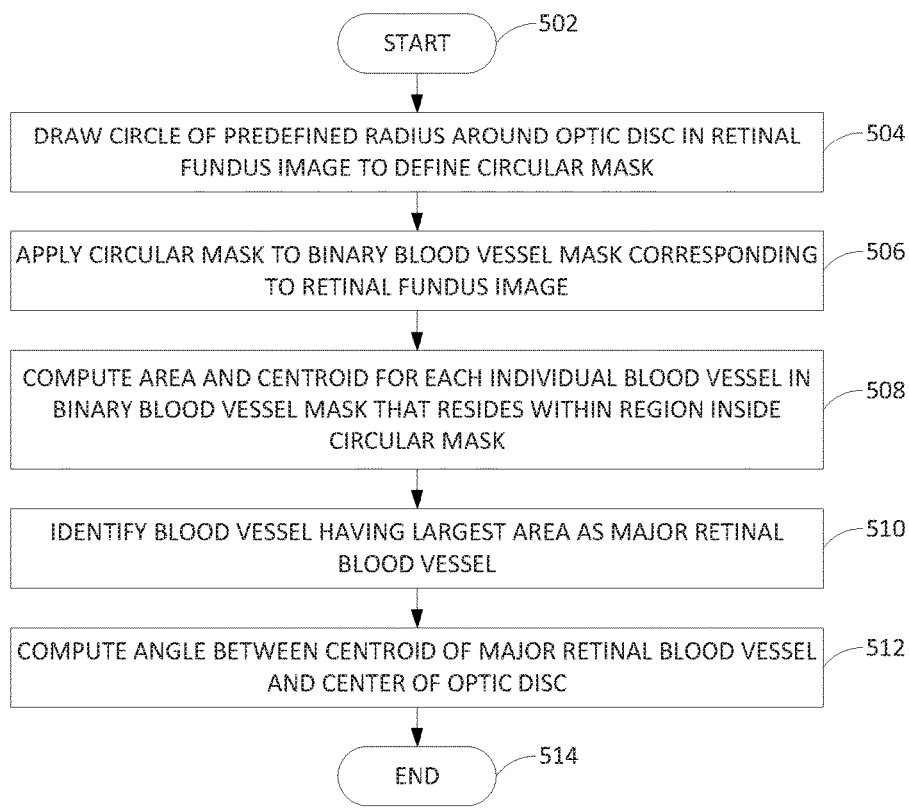
FIG. 5 is a flow diagram illustrating one example of a method for identifying and detecting the orientation of a major retinal blood vessel in a retinal fundus image, according to the present disclosure.

FIG. 5 is a flow diagram illustrating one example of a method 500 for identifying and detecting the orientation of a major retinal blood vessel in a retinal fundus image, according to the present disclosure. The method 500 exploits the fact that the orientation of the major blood vessel with respect to the optic disc is different for the left eye and the right eye.

The method 500 may be performed, for example, by the feature extractor 108 of the eye type detector 100 (e.g., in conjunction with step 210 of the method 200). As such, and for the sake of example, reference is made in the discussion of the method 500 to the feature extractor 108. However, the method 500 could also be performed by a different component of the eye type detector 100, or by a different system entirely. Thus, the references to the feature extractor 108 in the following discussion are not intended to be limiting.

The method 500 begins in step 502. In step 504, the feature extractor 108 draws a circle of a predefined radius around the optic disc in the retinal fundus image. In one example, the predefined radius is 200 pixels, and the circle is centered on the center of the optic disc. In a further example, the boundary of the circle is then eroded by a predefined number of pixels (e.g., fifty pixels). The resultant circular mask can be used to obtain the blood vessels outside the optic disc.

In step 506, the feature extractor 108 applies (e.g., superimposes) the circular mask created in step 504 to the binary blood vessel mask corresponding to the retinal fundus image.

In step 508, the feature extractor 108 detects each individual blood vessel in the binary blood vessel mask that resides within the region inside the circular mask and computes the area and centroid for each blood vessel.

In step 510, the feature extractor 108 identifies the blood vessel for which the largest area was computed in step 508 and designates this blood vessel as the major retinal blood vessel.

In step 512, the feature extractor 108 computes the angle between the center of the optic disc and the centroid of the major retinal blood vessel. This angle helps to identify the orientation of the major retinal blood vessel with respect to the optic disc.

The method 500 ends in step 514.

Figure 6:
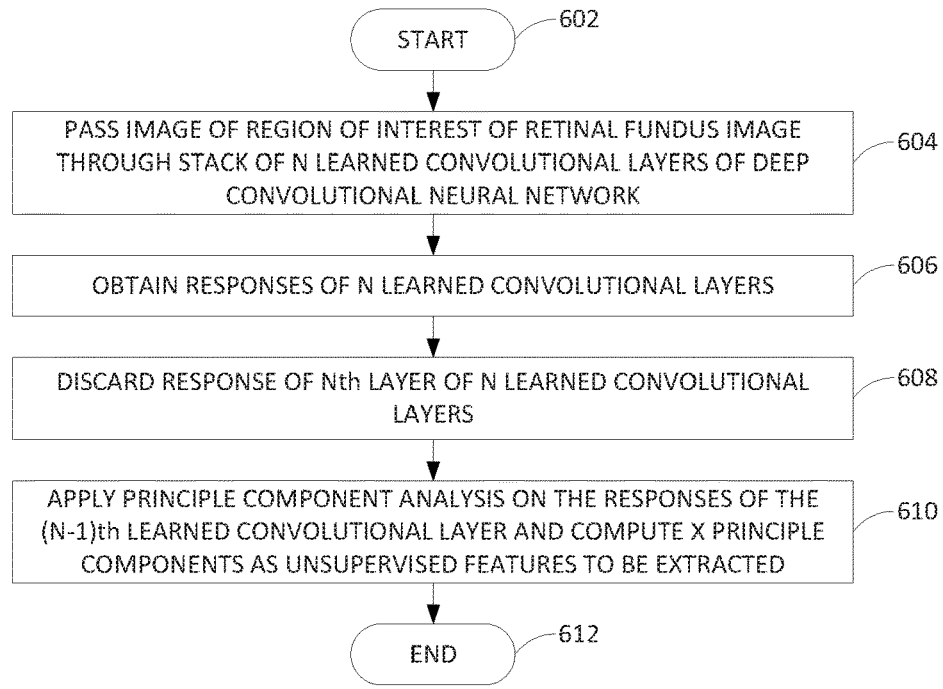
FIG. 6 is a flow diagram illustrating one example of a method for evaluating the response of a deep convolutional neural network to a retinal fundus image, according to the present disclosure.

FIG. 6 is a flow diagram illustrating one example of a method 600 for evaluating the response of a deep convolutional neural network to a retinal fundus image, according to the present disclosure. In one example, the method 600 assumes that the deep convolutional neural network has been trained on a training dataset of retinal fundus images to compute unsupervised features.

The method 600 may be performed, for example, by the feature extractor 108 of the eye type detector 100 (e.g., in conjunction with step 210 of the method 200). As such, and for the sake of example, reference is made in the discussion of the method 600 to the feature extractor 108. However, the method 600 could also be performed by a different component of the eye type detector 100, or by a different system entirely. Thus, the references to the feature extractor 108 in the following discussion are not intended to be limiting.

The method 600 begins in step 602. In step 604, the feature extractor 108 passes an image of the region of interest that has been cropped from the retinal fundus image (e.g., as defined in step 304 of the method 300) through the stack of learned convolutional/weight layers of the deep convolutional neural network. In one example, the deep convolutional neural network includes N learned convolutional layers. In a further example, N=sixteen.

In step 606, the feature extractor 108 obtains the responses of the N learned convolutional layers.

In step 608, the feature extractor 108 discards the response of the last or Nth learned convolutional layer. In one example, the Nth learned convolutional layer is specifically trained for approximately one thousand classes of the training dataset, while the (N−1)th learned convolutional layer generates approximately 4096 responses as the unsupervised features.

In step 610, the feature extractor 108 applies principle component analysis (PCA) on the responses of the (N−1)th learned convolutional layer, and computes x principle components as the unsupervised feature to be extracted, where x is predefined empirically. In one example, x is three.

The method 600 ends in step 612.

The flowchart and block diagrams in the Figures illustrate the architecture, functionality, and operation of possible implementations of systems and methods according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

Examples of the present disclosure may be a system, a computer-implemented method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
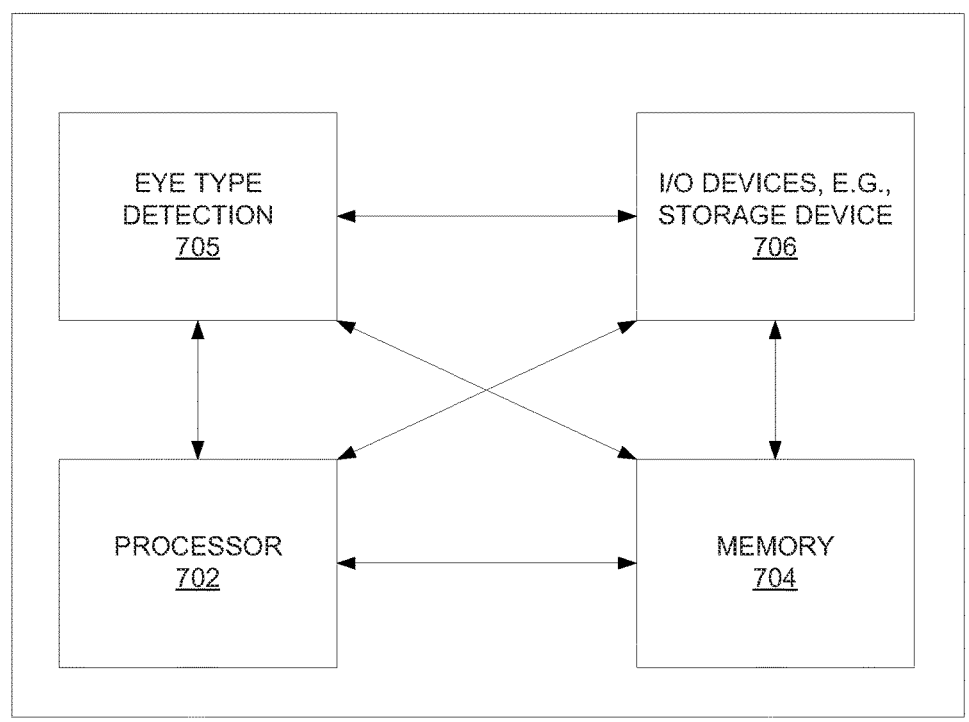
FIG. 7 depicts a high-level block diagram of a computer that can be transformed into a machine capable of performing the functions described herein.

FIG. 7, for example, depicts a high-level block diagram of a computer 700 that can be transformed into a machine capable of performing the functions described herein. The computer 700 may comprise, for example, part of the eye type detector 100 discussed above in connection with FIG. 1. Notably, no computer or machine currently exists that performs the functions as described herein. As a result, the examples of the present disclosure improve the operation and functioning of the general-purpose computer to automatically detect eye type in retinal fundus images, as disclosed herein.

As depicted in FIG. 7, the computer or system 700 comprises a hardware processor element 702 (e.g., a central processing unit (CPU), a microprocessor, or a multi-core processor), a memory 704, e.g., random access memory (RAM) and/or read only memory (ROM), a module 705 for automatically detecting eye type in retinal fundus images, and various input/output devices 706 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the general-purpose computer may employ a plurality of processor elements. Furthermore, although only one general-purpose computer is shown in the figure, if the method(s) as discussed above is implemented in a distributed manner for a particular illustrative example, i.e., the steps of the above method(s) or the entire method(s) are implemented across multiple general-purpose computers, then the general-purpose computer of this figure is intended to represent each of those multiple general-purpose computers.

It should be noted that the present disclosure can be implemented in software and/or in a combination of software and hardware, e.g., using application specific integrated circuits (ASIC), a general purpose computer or any other hardware equivalents, e.g., computer readable instructions pertaining to the respective systems and/or methods discussed above can be used to configure a hardware processor to perform the steps functions and/or operations of the above disclosed systems and methods. In one embodiment, instructions and data for the present module or process 705 for automatically detecting eye type in retinal fundus images (e.g., a software program comprising computer-executable instructions) can be loaded into memory 704 and executed by hardware processor element 702 to implement the steps, functions or operations as discussed above in connection with the exemplary system 100 and/or methods 200-600. The processor executing the computer readable or software instructions relating to the above described method(s) can be perceived as a programmed processor or a specialized processor. As such, the present module 705 for automatically detecting eye type in retinal fundus images (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server. In addition, it should be noted that the hardware processor can be configured or programmed to cause other devices to perform one or more operations as discussed above. In other words, the hardware processor may serve the function of a central controller directing other devices to perform the one or more operations as discussed above.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A computer-implemented method, comprising:
obtaining an image of a retinal fundus;
extracting a supervised feature of the retinal fundus based on anatomical domain knowledge of the retinal fundus from the image of the retinal fundus;
deriving an unsupervised feature of the retinal fundus from a response of a pre-trained deep convolutional neural network to at least a portion of the image of the retinal fundus, wherein the deriving comprises:
passing an image of a region of interest that has been cropped from the image of the retinal fundus through a stack of N learned convolutional layers of the pre-trained deep convolutional neural network, wherein N is a whole number between one and sixteen;
applying principal component analysis on responses of an (N−1)th layer of the N learned convolutional layers while discarding a response of an Nth layer of the N learned convolutional layers, wherein the Nth layer is trained for one thousand classes of a training dataset, and the (N−1)th layer generates more than four thousand responses as potential unsupervised features; and
extracting the unsupervised feature from a set of principal components obtained by the applying; and
determining whether the retinal fundus belongs to a left eye or a right eye, based on an analysis of a combination of the supervised feature and the unsupervised feature.

2. The computer-implemented method of claim 1, wherein the supervised feature comprises a cross-sectional vote-based probability score for the image of the retinal fundus.

3. The computer-implemented method of claim 2, wherein the extracting the supervised feature comprises:
cropping a region of interest from the image of the retinal fundus;
defining a search region within the region of interest;
defining a plurality of horizontal cross sections with the search region;
generating a plurality of votes for the plurality of horizontal cross sections, wherein a given vote of the plurality of votes indicates whether a corresponding cross section of the plurality of horizontal cross sections likely depicts the left eye or the right eye; and computing a probability score for the image of the retinal fundus, based on the plurality of votes.

4. The computer-implemented method of claim 3, wherein the region of interest is centered on an optic disc depicted in the image of the retinal fundus.

5. The computer-implemented method of claim 4, wherein the search region extends a predefined number above pixels above and below a center of the optic disc.

6. The computer-implemented method of claim 3, wherein the generating comprises, for a given cross section of the plurality of horizontal cross sections:

smoothing a pixel intensity distribution along the given cross section;

computing a peak point of the pixel intensity distribution, subsequent to the smoothing;

voting for the left eye when the peak point is located to the right of a center of an optic disc depicted in the image of the retinal fundus; and voting for the right eye when the peak point is located to the left of the center of the optic disc.

7. The computer-implemented method of claim 6, wherein the center of the optic disc is identified by performing operations comprising:

identifying a start point of the optic disc in the given cross section as a highest point along a gradient of pixel intensity values in the image of the retinal fundus;

identifying an end point of the optic disc in the given cross section as a lowest point along the gradient of pixel intensity values; and designating a middle point between the start point and the end point as the center of the optic disc for the given cross section.

8. The computer-implemented method of claim 1, wherein the supervised feature comprises relative blood vessel densities on the left side and the right side of an optic disc depicted in the image of the retinal fundus.

9. The computer-implemented method of claim 8, wherein the extracting the supervised feature comprises:

dividing a blood vessel mask image corresponding to the image of the retinal fundus into two parts, based on a location of a center of the optic disc, where a first part of the two parts depicts the left side of the optic disc, and a second part of the two parts depicts the right side of the optic disc; and computing the relative blood vessel densities for the two parts.

10. The computer-implemented method of claim 1, wherein the supervised feature comprises an orientation of a major retinal blood vessel with respect to an optic disc depicted in the image of the retinal fundus.

11. The computer-implemented method of claim 10, wherein the extracting the supervised feature comprises:

applying an optic disc-centered mask to a binary blood vessel mask corresponding to the image of the retinal fundus;

detecting individual blood vessels in the binary blood vessel mask that reside within a region inside the optic disc-centered mask;

computing an area and a centroid for each blood vessel of the individual blood vessels;

deriving the orientation from an angle between a center of the optic disc and the centroid of the blood vessel of the individual blood vessels for which the area is largest.

12. The computer-implemented method of claim 11, wherein the optic-disc centered mask is obtained by performing operations comprising:

drawing a circle of a predefined radius around the optic disc in the image of the retinal fundus, wherein the circle defines the optic disc-centered mask.

13. The computer-implemented method of claim 1, wherein the determining is performed using a support vector machine that has been trained using a plurality of features including the supervised feature and the unsupervised feature.

14. The computer-implemented method of claim 1, wherein the supervised feature is extracted from an image of retinal blood vessels that has been segmented from the image of the retinal fundus.

15. The computer-implemented method of claim 4, further comprising locating a position of the optic disc in the image of the retinal fundus by:

generating a green channel retinal image from the image of the retinal fundus;

applying a plurality of non-overlapping sliding windows on the green channel retinal image and on a binary blood vessel mask corresponding to the green channel retinal image; and selecting a location of a sliding window of the plurality of sliding windows that has a maximum blood vessel density and a maximum intensity value as the position of the optic disc.

16. The computer-implemented method of claim 4, wherein an index of a starting cross section of the plurality of horizontal cross sections is $R_{c-n}$, an index of an ending cross section of the plurality of horizontal cross sections is $R_{c+n}$, c is an index of a cross section of the plurality of horizontal cross sections that passes through a center of the optic disc, $n=r*a$, $a=0.65$, and n is smaller than r.

17. The computer-implemented method of claim 6, wherein the cross-sectional vote-based probability score is computed by:

repeating the smoothing, the computing the peak point, the voting for the left eye, and the voting for the right eye for every cross section of the plurality of horizontal cross sections, to generate a plurality of votes; and computing the cross-sectional vote-based probability score for the left eye as a percentage of the plurality of votes that favors the left eye; and computing the cross-sectional vote-based probability score for the right eye as a percentage of the plurality of votes that favors the right eye.

18. The computer-implemented method of claim 13, wherein parameters of the support vector machine comprise C, degree, gamma, kernel, and tolerance, and the parameters are computed using a five-fold cross validation accuracy-based grid search over a validation dataset.

19. A non-transitory machine-readable storage medium encoded with instructions executable by a processor, wherein the instructions cause the processor to perform operations comprising:

obtaining an image of a retinal fundus;

extracting a supervised feature of the retinal fundus based on anatomical domain knowledge of the retinal fundus from the image of the retinal fundus;

deriving an unsupervised feature of the retinal fundus from a response of a pre-trained deep convolutional neural network to at least a portion of the image of the retinal fundus, wherein the deriving comprises:

passing an image of a region of interest that has been cropped from the image of the retinal fundus through a stack of N learned convolutional layers of the pre-trained deep convolutional neural network, wherein N is a whole number between one and sixteen;

applying principal component analysis on responses of an (N−1)th layer of the N learned convolutional layers while discarding a response of an Nth layer of the N learned convolutional layers, wherein the Nth layer is trained for one thousand classes of a training dataset, and the (N−1)th layer generates more than four thousand responses as potential unsupervised features; and extracting the unsupervised feature from a set of principal components obtained by the applying; and determining whether the retinal fundus belongs to a left eye or a right eye, based on an analysis of a combination of the supervised feature and the unsupervised feature.

\* \* \* \* \*